(12) United States Patent
Joseph et al.

(10) Patent No.: US 9,518,972 B2
(45) Date of Patent: Dec. 13, 2016

(54) METHODS FOR DETECTING BACTERIAL INFECTIONS

(71) Applicants: AVISA PHARMA INC., Albuquerque, NM (US); SOUTHWEST SCIENCES, INC., Santa Fe, NM (US)

(72) Inventors: David S. Joseph, Santa Fe, NM (US); Steven M. Massick, Placitas, NM (US); Kristen A. Peterson, Santa Fe, NM (US); Anthony L. Gomez, Santa Fe, NM (US); Joel A. Silver, Santa Fe, NM (US)

(73) Assignees: Avisa Pharma, Inc., Alburquerque, NM (US); Southwest Sciences, Inc., Santa Fe, NM (US)

( * ) Notice: Subject to any disclaimer, the term of this patent is extended or adjusted under 35 U.S.C. 154(b) by 507 days.

(21) Appl. No.: 14/045,856

(22) Filed: Oct. 4, 2013

(65) Prior Publication Data
US 2014/0114206 A1    Apr. 24, 2014

Related U.S. Application Data

(60) Provisional application No. 61/715,992, filed on Oct. 19, 2012.

(51) Int. Cl.
| | |
|---|---|
| *A61B 5/08* | (2006.01) |
| *G01N 33/00* | (2006.01) |
| *A61B 5/097* | (2006.01) |
| *A61B 5/00* | (2006.01) |
| *A61K 51/12* | (2006.01) |
| *G01N 33/497* | (2006.01) |
| *C12Q 1/02* | (2006.01) |
| *G01N 33/569* | (2006.01) |

(52) U.S. Cl.
CPC ........... *G01N 33/0055* (2013.01); *A61B 5/082* (2013.01); *A61B 5/097* (2013.01); *A61B 5/42* (2013.01); *A61K 51/1206* (2013.01); *C12Q 1/02* (2013.01); *G01N 33/497* (2013.01); *G01N 33/569* (2013.01); *G01N 2458/15* (2013.01)

(58) Field of Classification Search
None
See application file for complete search history.

(56) References Cited

U.S. PATENT DOCUMENTS

| | | | |
|---|---|---|---|
| 5,317,156 A | 5/1994 | Cooper et al. | |
| 5,929,442 A | 7/1999 | Higashi | |
| 5,957,858 A | 9/1999 | Micheels et al. | |
| 6,486,474 B1 | 11/2002 | Owen et al. | |
| 6,778,269 B2 | 8/2004 | Fink et al. | |
| 6,800,855 B1 * | 10/2004 | Dong | G01N 21/39 |
| | | | 250/339.13 |
| 7,717,857 B2 * | 5/2010 | Timmins | A61K 51/04 |
| | | | 600/529 |
| 2008/0064975 A1 | 3/2008 | Hancock et al. | |
| 2008/0305050 A1 | 12/2008 | Timmins et al. | |
| 2012/0298868 A1 * | 11/2012 | Massick | G01N 21/3504 |
| | | | 250/339.13 |
| 2014/0179809 A1 * | 6/2014 | Perkett | G01N 21/39 |
| | | | 514/789 |

FOREIGN PATENT DOCUMENTS

| | | |
|---|---|---|
| WO | WO 2008/057662 A2 | 5/2008 |
| WO | WO 2009/101374 A1 | 8/2009 |
| WO | WO 2012/162695 | 11/2012 |
| WO | WO 2014/062392 | 4/2014 |

OTHER PUBLICATIONS

Harde H. et al. Opto-Acoustic 13C Breath Test Analyzer. Proc of SPIE vol. 7564(Photons Plus Ultrasound)1-7, 2010.*
Bell et al, 14C-urea Breath Analysis, A Non-Invasive Test for Campylobacter Pylori in the Stomach. The Lancet, Jun. 1987, 1(8546), 1367-1368.
Castrillo, A., et al., "Measuring the 13C/12C Isotope Ratio in Atmospheric C02 by Means of Laser Absorption Spectrometry: A New Perspective Based on a 2.05-µm diode laser", Isotopes in Environmental and Health Studies, Mar. 2006, 42(1), 47-56.
Chleboun, J. and P. Kocna, "Isotope Selective Nondispersive Infrared Spectrometry can Compete With Isotope Ratio Mass Spectrometry in Cumulative 13C02 Breath Tests: Assessment of Accuracy", Kin. Biochem. Metab., Feb. 2005. 13(34), 92-97.
Gagliardi, G., et al., High-Precision Determination of the 13C02/12C02 Isotope Ratio Using a Portable 2.008-µm diode-laser spectrometer, Published online: Aug. 12, 2003, Appl. Phys. B, 2003, 77, 119-124.
Horner, G., et al., "Isotope Selective Analysis of C02 With Tunable Diode Laser (TDL) Spectroscopy in the NIR", Analyst, Jul. 2004, 129, 772-778.
Hovde, D.C., et al., "Trace Gas Detection Using Vertical Cavity Surface Emitting Lasers. In Optical Remote Sensing for Environmental and Process Monitoring", Sep. 25-27, 1995, San Francisco, CA.
International Patent Application No. PCT/US2013/063365: International Search Report and the Written Opinion dated Jan. 24, 2014, 17 pages.
Wahl, E.H., et al., Applications of Cavity Ring-Down Spectroscopy to High Precision Isotope Ratio Measurement of 13C 12C in Carbon Dioxide, Isotopes in Environmental and Health Studies, Mar. 2006, 42(1), 21-35.
Wang, C. & Sahay, P., "Breath Analysis Using Laser Spectorscopic Techniques: Breath Biomarkers, Spectral Fingerprints, and Detection Limits", Sensors, 9(10), Oct. 19, 2009, 8230-8262.

* cited by examiner

*Primary Examiner* — Ralph Gitomer
(74) *Attorney, Agent, or Firm* — Baker & Hostetler LLP

(57) ABSTRACT

The invention is directed to methods of detecting lung, gastrointestinal tract, and systemic infections by measuring $^{13}CO_2/^{12}CO_2$ isotopic ratios of gaseous carbon dioxide in exhaled breath samples of a subject after administration of a $^{13}C$-isotopically-labeled compound.

24 Claims, 1 Drawing Sheet

METHODS FOR DETECTING BACTERIAL INFECTIONS

CROSS REFERENCE TO RELATED APPLICATIONS

This application claims the benefit of U.S. Provisional Application No. 61/715,992, filed Oct. 19, 2012, the entirety of which is incorporated by reference herein.

JOINT RESEARCH AGREEMENT

The claimed inventions were made under a joint research agreement between Southwest Sciences Incorporated and Avisa Pharma, Inc. The joint research agreement was in effect on or before the date the claimed inventions were made and the claimed inventions were made as a result of activities undertaken within the scope of the joint research agreement.

TECHNICAL FIELD

The invention is directed to methods of detecting lung, gastrointestinal tract, and systemic infections.

BACKGROUND

Detecting whether a patient has a bacterial infection is important in providing suitable treatment for the patient. Often, this detection can be difficult because of the infection's location, for example, in the lungs or gastrointestinal tract. Methods of detecting the presence of bacteria by measuring isotopically-labeled ratios of volatile gases has been reported. See, e.g., U.S. Pat. No. 7,717,857. Faster methods of detecting those ratios are still needed. Portable machines that can accurately detect those ratios are also still needed.

SUMMARY

Methods for determining the present or absence of a bacterial infection in a subject are provided. These compare administering to the subject an effective amount of a $^{13}$C-isotopically-labeled compound that produces $^{13}CO_2$ upon bacterial metabolism. The methods further include collecting at least one sample of exhaled breath from the subject and conducting the sample to a sample chamber of a detection apparatus. A laser light source of the detection apparatus is then actuated to emit one or more of the wavelength pairs 2054.37 and 2052.42; 2054.96 and 2051.67; or 2760.53 and 2760.08 nanometers and the laser light thus actuated is directed through the sample in the sample chamber to impinge upon a detector for such wavelengths. The isotopic ratio of $^{13}CO_2$ to $^{12}CO_2$ present in the sample is ascertained, allowing information about bacterial infection of the subject to be determined

DETAILED DESCRIPTION OF ILLUSTRATIVE EMBODIMENTS

Figure 1:
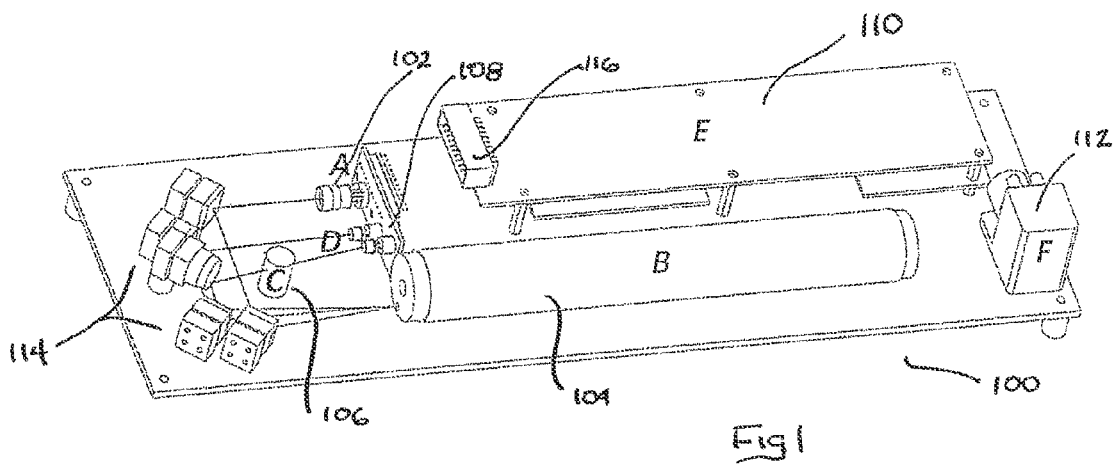
FIG. 1 is a plan view of an exemplary laser absorbance device for use in accordance with some embodiments of this invention.

The invention is directed to methods for determining the presence or absence of a bacterial infection in a subject. The bacterial infection can be localized in any organ or system of the subject including, for example, the lungs or the gastrointestinal tract. Systemic bacterial infections can also be detected using the methods described herein.

Any bacteria that can convert the $^{13}$C-isotopically-labeled compounds of the invention into $^{13}CO_2$ can be detected using the methods of the invention. Examples of such bacteria include *Pseudomonas aeruginosa, Staphylococcus aureus, Mycobacterium tuberculosis, Acenitobacter baumannii, Klebsiella pneumonia, Francisella tularenis, Proteus mirabilis, Aspergillus* species, and *Clostridium difficile*.

The methods of the invention include administering to the subject, an effective amount of a $^{13}$C-isotopically-labeled compound that produces $^{13}CO_2$ upon bacterial metabolism. Exemplary examples of such compounds include isotopically labeled urea, isotopically labeled glycine, isotopically labeled citrulline, or a mixture thereof. Other preferred compounds include isotopically-labeled tyrosine, isotopically-labeled p-hydroxyphenylacetic acid, or a mixture thereof. Administration of the $^{13}$C-isotopically-labeled compound can be achieved by any known means. Preferred methods of administration include inhalation and ingestion. Administration via injection, i.e., intramuscular, subcutaneous, peritoneal, and intradermal injection, is also within the scope of the invention.

Within the scope of the invention, one or more exhaled breath samples from the subject can be collected before administration of the $^{13}$C-isotopically-labeled compound. Such samples can be used as controls in the methods of the invention.

Following a suitable time period after administration of the $^{13}$C-isotopically-labeled compound, one or more samples of exhaled breath are collected from the subject. A "suitable time period" refers to the length of time required for the compound to be converted to carbon dioxide by a bacteria. Preferably, the samples are collected after no more than 40-70 minutes following administration.

Samples can be collected in any vessel suitable for containing samples of exhaled breath, for example, a bag or vial. Samples may also be directly exhaled into the device by using a suitable mouthpiece. Samples can also be directed exhaled into the device by being collected using a nasal cannula from a suitable port on other respiratory equipment, for example, a ventilator.

The samples are analyzed to determine the isotopic ratio of $^{13}CO_2$ to $^{12}CO_2$ in the samples. Preferably, at least a majority of the exhaled breaths, and most preferably every exhaled breath, is sampled for a given time period or until the determination of the level of activity has reached a preset accuracy.

The sample is conducted to a sample chamber of a detection apparatus. A laser light source of the detection apparatus is actuated to emit one or more of the wavelength pairs 2054.37 and 2052.42; 2054.96 and 2051.67; or 2760.53 and 2760.08 nanometers. The laser light thus actuated is directed through the sample in the sample chamber to impinge upon a detector for such wavelengths. The isotopic ratio of $^{13}CO_2$ to $^{12}CO_2$ present in the sample can then be ascertained.

A graph or curve may be generated showing the ratio of $^{13}CO_2$ to $^{12}CO_2$ in the breath of the tested subject as a function of time. A curve showing an increase in the ratio of $^{13}CO_2$ to $^{12}CO_2$ over time is evidence of the existence of a bacterial infection.

The concentrations or amounts (ratio) of $^{13}CO_2$ to $^{12}CO_2$ is compared to a standard concentration (ratio) of $^{13}CO_2$ to $^{12}CO_2$ in a healthy subject and a curve is conveniently generated. From the curve, the presence or absence of a bacterial infection may be determined or diagnosed directly. Other methods for comparing the output ratio to ratios expected from healthy subjects may also be employed.

In exemplary embodiments, a curve may be fitted to these measured concentrations and is then analyzed, preferably by determining the rate of rise of the curve. Such an analysis (rising rate) indicates the level of activity of bacterial infection in the subject, which can be used to diagnose the presence and extent of an infection in the subject. This same approach may be used, with modification, to determine the effectiveness of therapy of an infection and the prognosis for inhibition and/or a cure of infection.

Within the scope of the invention are methods of detecting the presence or absence of a bacterial infection in a subject by comparing the isotopic ratio of $^{13}CO_2$ to $^{12}CO_2$ in the exhaled breath samples obtained after administration of the $^{13}C$-isotopically labeled compound to the isotopic ratio of $^{13}CO_2$ to $^{12}CO_2$ in an exhaled breath sample obtained from the subject prior to the administration of the $^{13}C$-isotopically labeled compound.

Within the scope of the invention, an increase in the ratio of $^{13}CO_2$ to $^{12}CO_2$ in the exhaled breath samples obtained after inhalation of the $^{13}C$-isotopically labeled compound to the isotopic ratio of $^{13}CO_2$ to $^{12}CO_2$ in the exhaled breath sample obtained from the subject prior to the inhalation of the $^{13}C$-isotopically labeled compound indicates the presence of a bacterial lung infection.

In addition, an increase in the ratio of $^{13}CO_2$ to $^{12}CO_2$ in the exhaled breath samples obtained after ingestion of the $^{13}C$-isotopically labeled compound to the isotopic ratio of $^{13}CO_2$ to $^{12}CO_2$ in the exhaled breath sample obtained from the subject prior to the ingestion of the $^{13}C$-isotopically labeled compound indicates the presence of a bacterial gastrointestinal tract infection.

Also, an increase in the ratio of $^{13}CO_2$ to $^{12}CO_2$ in the exhaled breath samples obtained after infection of the $^{13}C$-isotopically labeled compound to the isotopic ratio of $^{13}CO_2$ to $^{12}CO_2$ in the exhaled breath sample obtained from the subject prior to the injection of the $^{13}C$-isotopically labeled compound indicates the presence of a bacterial systemic infection.

Detection apparatuses useful in the present invention will include a sample chamber, into which breath samples can be conducted. These devices will also include a laser light source actuated to emit one or more of the wavelength pairs 2054.37 and 2052.42; 2054.96 and 2051.67; or 2760.53 and 2760.08 nanometers. These devices will also include a detector for detection of one or more of the wavelength pairs.

The detection apparatuses useful in the present invention can include small, extremely low power, near infrared diode lasers to attain field portable, battery operated $\delta^{13}CO_2$ measurement instruments with high degrees of accuracy and sensitivity. These devices and the methodologies which employ them may be used to determine $\delta^{13}CO_2$ in exhaled breath samples of subjects having, or suspected of having, a bacterial infection.

Preferred detection apparatuses will analyze carbon isotope ratios in exhaled carbon dioxide samples without being adversely affected by temperature changes. The accuracy and precision of measuring carbon dioxide isotope ratios can be affected by changes in the ground state population of carbon dioxide. The origins of the isotopic differences in samples may be diverse and are not the subject of the present invention. Rather, it is recognized that ascertaining the value of the isotopic ratio is inherently important and commercially useful.

Optical absorption spectroscopy is based on the well-known Beer-Lambert Law. Gas concentrations are determined by measuring the change in the laser beam intensity, $I_0$, due to optical absorption of the beam by a sample of the gas. If a sample cell is used for the analysis, such that the path length of the beam and inherent characteristics of the measuring device are constant, absorbance measurements allow calculation of the gas number density, n, or gas concentration.

Gas phase diode laser absorption measurements interrogate individual absorption lines of gas molecules. These absorption lines correspond to the transition of the gas molecule, e.g. carbon dioxide, from a ground energy state to a higher excited energy state by absorption of a photon of light. The lines are typically quite narrow at reduced sample gas pressure thereby permitting selective detection of a gas in the presence of other background gases such as water vapor. The isotopes of $CO_2$ have distinct absorption lines that occur at shifted wavelengths with respect to each other due to the mass difference between $^{12}C$ and $^{13}C$.

Absorbance measurements are affected by the gas temperature and the magnitude of this temperature sensitivity varies depending on absorption line selection and the total ground state energy of the optical transition. A collection of molecules at room temperature is distributed over many discrete molecular energy states that vary in total energy according to how fast the molecules rotate and vibrate. That is, the ground state molecular population is distributed about discrete rotational and vibrational energy states according to a Boltzmann distribution.

A temperature dependence of $\Delta\delta^{13}CO_2$ can affect the long term stability and sensitivity of diode laser based isotopic measurements of carbon dioxide. [references 2-6] $^{13}CO_2$ and $^{12}CO_2$ absorption lines with near equal ground state energies can be useful in attaining relative temperature insensitivity for isotopic ratio measurements.

Vertical cavity surface emitting lasers (VCSELs) have been shown to attain scan ranges of 10 to 15 cm$^{-1}$. These have been used to give rise to rugged, high precision field instruments as exemplified by a laser hygrometer manufactured by Southwest Sciences, Inc and a handheld methane leak detector manufactured by the Southern Cross Company. Accordingly, for certain apparatuses for use in the invention, VCSELs can be used that may be scanned over the desired spectral wavelengths, at a useful scan rate in the context of an overall testing apparatus as to give rise to some or all of the desired benefits of the present invention. In some embodiments, the VCSEL devices are caused to scan in the kilohertz scan rate or greater over approximately 10 cm$^{-1}$ ranges.

Suitable laser sources may also be formed from a plurality, usually a pair of laser emitters. Such emitters may be fabricated to emit at one of the preferred wavelengths of a wavelength pair. VCSEL devices useful in the invention may be ordered from Vertilas GmbH of Germany and can also be made by other sources of laser emitters.

Pairs of $^{13}CO_2$ and $^{12}CO_2$ spectral lines have been identified, each pair of which has near zero ground state energy difference, a line separation less than 12 cm$^{-1}$, and is substantially free of water interference. It is now been discovered that these pairs of lines are highly useful in the ascertainment of $^{13}CO_2/^{12}CO_2$ isotopic ratios in gas samples. The temperature dependence of measurement using these pairs is desirably low.

The spectral line pairs as follows are highly useful in making carbon dioxide isotopic absorption measurements using VCSELs in gas cells in analyzing exhaled breath samples:

| $^{12}CO_2$ wavelength (nm) | $^{13}CO_2$ wavelength (nm) |
|---|---|
| 2054.37 | 2052.42 |
| 2054.96 | 2051.67 |
| 2760.53 | 2760.08 |

It will be appreciated that the wavelengths identified in the foregoing line pairs are nominal and that some variation from the listed values may be useful. In this regard, it will be understood that useful wavelengths will be those which are sufficiently close to the recited values as to provide one or more of the benefits of the present invention. Thus, such wavelengths will confer either improved accuracy, improved temperature stability or another of the desirable properties set forth herein to the measurement of $CO_2$ isotopic ratios. In general, preferred wavelengths will be within 0.5 of a nanometer of the recited values.

In addition to the laser light source operating at the desired wavelengths, the apparatuses useful with the present invention include a sample container for holding the gas sample, which container is configured to provide a relatively long light path through the sample by way of mirrors. One or more signal detectors are included as is control circuitry for controlling the laser and for collecting and manipulating the output signal from the detector or detectors. Other equipment to facilitate sample collection, sample preparation, data interpretation and display and other things may also be included in systems and kits provided by this invention. All such components are preferably sufficiently rugged as to permit the deployment of the devices outside of a laboratory and even in a hand held context.

The present apparatuses are also useful in a system or kit. Components of the system or kit may include sample collection containers, such as gas tight bags, preferably ones featuring injection ports, syringes, and other items which facilitate sample collection and transfer to the sample chamber of the apparatus. Such sample collection elements may assume different configurations depending upon the source of the gas to be sampled. Thus, the same may, for example, be useful for collecting breath of a subject, such as when sampling headspace gases from the stomach of a subject.

Portable devices and systems are known having a general arrangement of elements suitable for us in some of the embodiments of the present invention. For example, the '96 Hawk hand-held methane leak detector system sold by Southern Cross Corp. provides sample container, mirror assemblies, power supply, sample handling and other components which may be adapted for use in the invention. Such systems, however, are not otherwise amenable for such use. Thus, the provision of diode laser sources which are capable of scanning the requisite spectral line pairs with effective frequency, stability and accuracy must be accomplished. Likewise, detectors for sensing optical absorption in the selected line pairs with needed accuracy as well as data collection, storage, manipulation and display or reporting devices and/or software is needed.

FIG. 1 depicts certain aspects of one device that can be used with the presenting invention. A $CO_2$ optical absorption measurement device is depicted 100, which comprises a diode laser source, mirrors 114, and gas sample chamber 104. Taken together, these form an optical path in conjunction with preferred reflective surfaces inside the sample chamber, not shown. The optical path, which is effectively many times longer than the physical length of the chamber, permits the enhanced absorption of laser light by gas samples in the chamber. One or more gas pumps, 112 are conveniently included to transport gas sample into and out of the sample chamber which may, likewise, be provided with one or more pressure gauges. Preferably, a reference gas chamber, 106 is also employed together with mirrors, 114 for directing laser light through the reference gas chamber 106. The light paths through the sample and reference chambers are directed to one or more detectors, 108 for assessing the intensity of laser light. Processor or processors in control module, 110 determine the amount of absorption of incident laser light by the sample in the sample chamber, by reference to the reference sample in the reference chamber. This determination may be performed by routine software of firmware, either on board the device or external to it. Preferably, electrical connections, 116 are provided enabling either signals or processed data from the device to be ported to external display or data collection and manipulation devices. In accordance with certain preferred embodiments, some or all of the elements making up apparatuses and systems of the invention and the functions they perform are operated under the control of a controller. Such controller, which may be on board the instrument or external to it, may be a general purpose digital computational device or a special purpose digital or digital-analog device or devices. Control by the controller may be of, for example, power supplies for the laser, detector, gas sample pump, processors and other components.

In operation, a gas sample suspected of containing carbon dioxide is placed into the sample chamber of the devices of the invention. The laser light source or sources is then caused to transit the sample chamber, preferably via a recurring pathway so as to increase the overall path length and improve the measurement sensitivity. The light source is then directed to one or more sensors and the sensor readings interpreted to give rise to a value for wavelength absorption by the sample. The methodologies for making this determination are well known in the art, and include, for example, direct absorption spectroscopy, wavelength modulation spectroscopy, cavity ringdown spectroscopy, and other alternatives By comparing the absorption of light having each of the chosen pair of wavelengths, values for the carbon 12 and carbon 13 isotopes in the carbon dioxide sample become known. Perforce, their ratio may be calculated. For some of the preferred embodiments of the invention, a reference gas sample is provided and the same irradiated, detected and the signal interpreted. The data thus obtained is used to standardize the data arising from irradiation of the sample chamber.

The mechanics of the apparatus including the supply of power to the laser light source or sources, to the detectors and to any data storage, presentation and manipulation elements is preferably under the control of a controller, whether digital or analog. A digital computer may also or in addition be used. Such computer may be on board or connected via a control interface.

It is preferred that determination of light absorption in accordance with the present invention be accomplished by wavelength modulation spectroscopy (WMS). While WMS has been used previously for $\delta^{13}CO_2$ measurements [17], it has never been performed for the line pairs that have now been determined to be used for isotopic ratios determinations in carbon dioxide.

WMS is preferred to direct absorption spectroscopy for use in the present invention, although direct measurement may be used if desired. For direct absorbance measurements the laser current is ramped so that the wavelength output is repeatedly scanned across a gas absorption line and the spectra generated are co-averaged. Analysis of direct absorption spectra involves detecting small changes on a large detector signal. For very low concentration changes this is problematic. To perform WMS, a small high-frequency sinusoidal modulation is superimposed on the diode laser current ramp. This current modulation produces a modulation of the laser wavelength at the same high frequency. Absorption by the target gas converts the wavelength modulation to an amplitude modulation of the laser intensity incident on the detector, adding AC components to the detector photocurrent. The detector photocurrent is demodulated at twice the modulation frequency, 2 f detection. This selectively amplifies only the AC components (a zero background measurement) and shifts the measurement from near DC to higher frequencies where laser noise is reduced. Spectral noise is greatly reduced by performing signal detection at frequencies (>10 kHz) high enough to avoid fluctuations in the laser output power, laser excess (1/f) noise. In carefully optimized laboratory setups, WMS has measured absorbances as low as $1\times10^{-7}$, which is near the detector noise limit. However, in compact field instrumentation, background artifacts typically limit the minimum detectable absorbance $\alpha_{min}$ to $1\times10^{-5}$ $s^{-1/2}$. The value for $\alpha_{min}$ can be improved by longer time averaging of the 2 f signal with the improvement scaling as $t^{1/2}$ for periods of 100 to 300 seconds.

Figure 2:
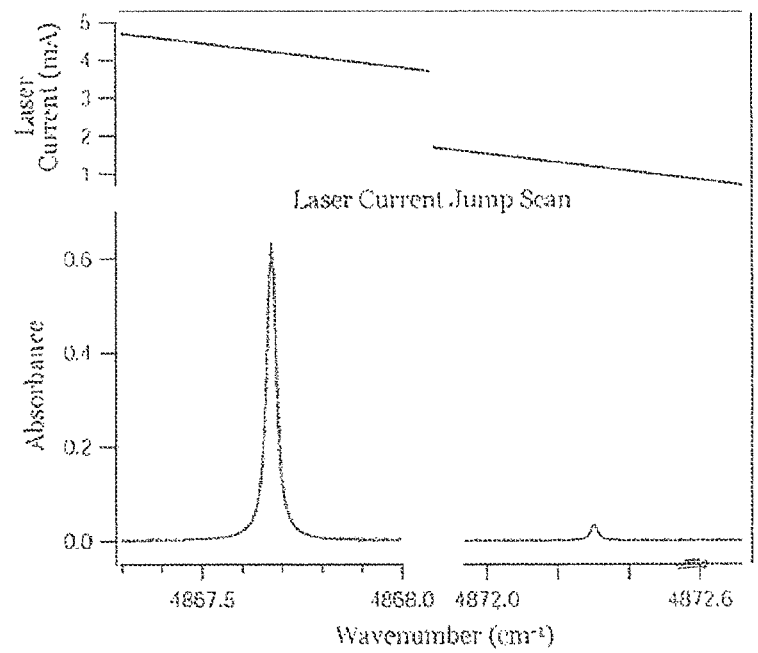
FIG. 2 illustrates a preferred jump scanning regime.

The $^{13}CO_2$ and $^{12}CO_2$ absorption line pairs described herein give rise to relatively temperature insensitive $\delta^{13}CO_2$ isotopic ratio determinations in gas samples are separated by several absorption lines that do not need to be measured. Instead of continuously scanning the laser wavelength between the two peaks of interest in each pair, the electronics is caused to operate the laser in a jump scan fashion. This is illustrated in FIG. 2. The laser current scan is programmed to have a discontinuity that will rapidly change the wavelength. The first few data points after the jump are preferably not used, as the laser wavelength may not be stable immediately after the current jump. VCSELs used in the present invention may be operated in this way even with four current jumps in order to measure five different absorption lines simultaneously with no undue reduction in sensitivity.

Compositions for oral administration or inhalation, i.e., pulmonary, administration are as otherwise described herein. Oral compositions include powders or granules, suspensions or solutions in water or non-aqueous media, sachets, capsules or tablets. Thickeners, diluents, flavorings, dispersing aids, emulsifiers or binders may be desirable. Compositions for pulmonary administration include a pharmaceutically acceptable carrier, additive or excipient, as well as a propellant and optionally, a solvent and/or a dispersant to facilitate pulmonary delivery to the subject.

Sterile compositions for injection can be prepared according to methods known in the art.

While the present invention has been set forth with reference to numerous embodiments and alternatives, the present specification is not to be taken to be limiting. The invention is solely measured by its claims.

REFERENCES

1. Bell, G. D., et al., *14C-urea breath analysis, a non-invasive test for Campylobacter pylori in the stomach.* Lancet, 1987. 1: p. 1367-1368.
2. Chelboun, J. and P. Kocna, *Isotope selective nondispersive infrared spectrometry can compete with isotope ratio mass spectrometry in cumulative 13CO2 breath tests: assessment of accuracy.* Kin. Biochem. Metab., 2005. 13(34): p. 92-97.
3. Castrillo, A., et al., *Measuring the 13C/12C isotope ratio in atmospheric CO2 by means of laser absorption spectrometry: a new perspective based on a 2.05-μm diode laser.* Isotopes in Environmental and Health Studies, 2006. 42(1): p. 47-56.
4. Gagliardi, G., et al., *High-precision determination of the 13CO2/12CO2 isotope ratio using a portable 2.008-μm diode-laser spectrometer.* Appl. Phys. B, 2003. 77: p. 119-124.
5. Homer, G., et al., *Isotope selective analysis of CO2 with tunable diode laser (TDL) spectroscopy in the NIR.* Analyst, 2004. 129: p. 772-778.
6. Wahl, E. H., et al., *Applications of cavity ring-down spectroscopy to high precision isotope ratio measurement of 13C 12C in carbon dioxide.* Isotopes in Environmental and Health Studies, 2006. 42: p. 21-35.
7. Hovde, D. C., et al. *Trace Gas Detection Using Vertical Cavity Surface Emitting Lasers.* in Optical Remote Sensing for Environmental and Process Monitoring. 1995. San Francisco, Calif.
8. U.S. Pat. No. 6,800,855
9. U.S. Pat. No. 5,929,442

What is claimed:

1. A method for determining the presence or absence of a bacterial lung infection in a subject comprising:
   administering to the subject, a $^{13}$C-isotopically-labeled compound that produces $^{13}CO_2$ upon bacterial metabolism;
   collecting at least one sample of exhaled breath from the subject;
   conducting the sample to a sample chamber of a detection apparatus;
   actuating a laser light source of the detection apparatus to emit one or more of the wavelength pairs 2054.37 and 2052.42; 2054.96 and 2051.67; or 2760.53 and 2760.08 nanometers;
   directing the laser light thus actuated through the sample in the sample chamber to impinge upon a detector for such wavelengths; and
   ascertaining the isotopic ratio of $^{13}CO_2$ to $^{12}CO_2$ present in the sample to determine the presence or absence of a bacterial lung infection in the subject.

2. The method of claim 1 further comprising comparing the isotopic ratio of the sample with the isotopic ratio of a control sample to effect said determination.

3. The method of claim 2, wherein the control sample comprises at least one sample of exhaled breath from the subject prior to administration of the $^{13}$C-isotopically-labeled compound.

4. The method of claim 2, wherein the control sample includes the isotopic ratio of $^{13}CO_2$ to $^{12}CO_2$ present in exhaled breath of a population that has not been administered the $^{13}$C-isotopically-labeled compound.

5. The method of claim 1, wherein the compound is isotopically labeled urea, isotopically labeled glycine, isotopically labeled citrulline, or mixture thereof.

6. The method of claim 1, wherein the $^{13}$C-isotopically-labeled compound is tyrosine, p-hydroxyphenylacetic acid, or a mixture thereof.

7. The method of claim 1, wherein the $^{13}$C-isotopically-labeled compound is administered by inhalation.

8. The method of claim 1, wherein the $^{13}$C-isotopically-labeled compound is administered by ingestion.

9. The method of claim 1, wherein the $^{13}$C-isotopically-labeled compound is administered by injection.

10. The method of claim 1, wherein the lungs are infected by *Pseudomonas aeruginosa, Staphylococcus aureus, Mycobacterium tuberculosis, Acenitobacter baumannii, Klebsiella pneumonia, Francisella tularenis, Proteus mirabilis, Aspergillus* species, or *Clostridium difficile*.

11. The method of claim 1, wherein the infection is a result of an infection from a bacteria having citrulline ureidase.

12. The method of claim 1, wherein the apparatus further comprises a processor for interpreting or presenting the signals received by the detector.

13. The method of claim 1, wherein the apparatus further comprises one or more of power supply, gas pump, pressure gauge, signal processor, and reference gas chamber.

14. The method of claim 1, wherein the laser light source of the apparatus scans the pair of wavelengths using wavelength modulation spectroscopy.

15. The method of claim 1, wherein the wavelength pair is 2054.37 and 2052.42 nanometers.

16. The method of claim 1, wherein the wavelength pair is 2051.67 and 2054.96 nanometers.

17. The method of claim 1, wherein the wavelength pair is 2760.53 and 2760.08 nanometers.

18. The method of claim 1, wherein the laser light source of the apparatus comprises a pair of laser emitters.

19. The method of claim 1, wherein the laser light source of the apparatus is a vertical cavity surface emitting laser.

20. The method of claim 1 wherein the isotopically labeled compound is $^{13}$C-labeled urea.

21. The method of claim 1 wherein the isotopically labeled compound is a mixture of $^{13}$C-labeled urea and $^{13}$C-labeled glycine.

22. The method of claim 1 wherein the bacterial lung infection is *Pseudomonas aeruginosa*.

23. The method of claim 1 further comprising comparing the isotopic ratio of $^{13}CO_2$ to $^{12}CO_2$ in the exhaled breath samples obtained after administration of the $^{13}$C-isotopically labeled compound to the isotopic ratio of $^{13}CO_2$ to $^{12}CO_2$ in an exhaled breath sample obtained from the subject prior to the administration of the $^{13}$C-isotopically labeled compound.

24. The method of claim 23, wherein an increase in the ratio of $^{13}CO_2$ to $^{12}CO_2$ in the exhaled breath samples obtained after inhalation of the $^{13}$C-isotopically labeled compound to the isotopic ratio of $^{13}CO_2$ to $^{12}CO_2$ in the exhaled breath sample obtained from the subject prior to the inhalation of the $^{13}$C-isotopically labeled compound indicates the presence of a bacterial lung infection.

* * * * *